United States Patent
Krouse et al.

(10) Patent No.: US 6,544,319 B1
(45) Date of Patent: Apr. 8, 2003

(54) PURIFICATION OF HEXAFLUORO-1,3-BUTADIENE

(75) Inventors: Steven Arnold Krouse, Tamaqua, PA (US); John Chodur, Nesquehoning, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/050,352

(22) Filed: Jan. 16, 2002

(51) Int. Cl.$^7$ .......................... B01D 53/04; C07C 17/38
(52) U.S. Cl. .............. 95/126; 95/131; 95/141; 95/148; 95/902; 570/179
(58) Field of Search .......................... 95/116, 117, 121, 95/126, 131, 141, 143–145, 148, 902; 570/179

(56) References Cited

U.S. PATENT DOCUMENTS

| | | | |
|---|---|---|---|
| 3,381,041 A | 4/1968 | Kometani et al. | 260/653 |
| 3,696,156 A | 10/1972 | Weeks | 260/648 F |
| 4,940,824 A | * 7/1990 | Yates | 570/179 |
| 5,300,714 A | 4/1994 | Pothapragada et al. | 570/179 |
| 5,507,941 A | 4/1996 | Pothapragada et al. | 210/94 |
| 5,810,910 A | 9/1998 | Ludwig et al. | 95/138 |
| 5,919,285 A | * 7/1999 | Li et al. | 95/45 |
| 6,187,077 B1 | * 2/2001 | Li | 95/47 |
| 6,274,782 B1 | * 8/2001 | Ohno et al. | 570/179 |
| 6,346,138 B1 | * 2/2002 | Holmer | 95/118 |

FOREIGN PATENT DOCUMENTS

| | | |
|---|---|---|
| EP | 0457613 | 3/1995 |
| JP | 10287595 | 10/1998 |

OTHER PUBLICATIONS

Miller, et al., JACS pp. 1767–1768 (Apr. 5, '61).
F.J. Weigert, 65 J.Fluorine Chem 67–71 (1993) "Interaction of perfluorocarbons with carbon."
Chambers, et al., 91 J.Fluorine Chem (63–68 (1998) "Reactions involving fluoride ion . . .".

* cited by examiner

Primary Examiner—David A. Simmons
Assistant Examiner—Frank M. Lawrence
(74) Attorney, Agent, or Firm—Geoffrey L. Chase

(57) ABSTRACT

An HFBD purification process includes: (a) contacting a composition containing HFBD with an adsorbent to remove from the HFBD at least two impurities selected from the group consisting of water, an alcohol, hydrofluoric acid and a fluorinated olefin, wherein the adsorbent is a solid having an average pore diameter of about 5 Å and the adsorbent is contacted with the HFBD at a rate of at least 2.7 kg of the HFBD per hour; and (b) recovering from the adsorbent a purified HFBD product containing at least 99.9 vol. % HFBD, a reduced amount of the impurities and less than 0.1 vol. % hexafluoro-2-butyne. Alternatively, the process can be conducted at any contacting rate to produce 99.96 vol. % HFBD. The process can also be conducted at any contacting rate in a bed within a column having a length of at least 30 cm and an inner diameter of at least 2.5 cm.

25 Claims, 2 Drawing Sheets

US 6,544,319 B1

PURIFICATION OF HEXAFLUORO-1,3-BUTADIENE

BACKGROUND OF THE INVENTION

This invention relates to a process for the purification of hexafluoro-1,3-butadiene, and more particularly to such a process employing an adsorbent to accomplish the desired purification.

Hexafluoro-1,3-butadiene (HFBD) is employed in the manufacture of semiconductors as an etchant for silicon oxide and related materials. HFBD employed in the semiconductor industry must be of extremely high purity. Commercially available HFBD is of 99.0 to 99.9 vol % purity, and contains a mixture of partially fluorinated and chlorinated isomers of butadiene, butadiene dimers, starting materials and solvents. The semiconductor industry requires HFBD of greater purity.

It is known to use adsorbents to remove perfluorinated olefinic impurities from perfluorinated, saturated compounds. For example, U.S. Pat. No. 3,696,156 discloses a process comprising the use of alumina for vapor phase removal of olefinic impurities from saturated fluoroperhalocarbons. The process is conducted in a temperature range from 180° C. to 250° C.

U.S. Pat. No. 5,300,714 and related patent documents U.S. Pat. No. 5,507,941 and EP 0457613B1 teach the removal of olefinic impurities from a saturated fluoroperhalocarbon liquid by contacting the liquid with alumina-type compounds at ambient temperatures. The use of 5 Å molecular sieve is disclosed; however, it exhibited the lowest efficiency for removing pefluoroisobutylene from perfluorinated alkane (33%) of any adsorbent shown in Table 3 of the '714 patent, other than the comparative example adsorbents. Liquid contact and temperatures above room temperature were required and no preferential removal of one olefinic impurity over another was reported. No mention was made of removing moisture, HF and/or iso-propyl alcohol, which are impurities specific to HFBD.

JP 10287595 discloses the use of adsorbents to remove $C_2$ hydrofluorocarbon impurities ($C_2$HFCs) from the saturated compound hexafluoroethane. Suitable adsorbents include zeolites having an average pore diameter of 3.5–11 Angstroms and a silica/alumina ratio less than or equal to 2.0; and carbonaceous adsorbents having an average pore diameter of 3.5–11 Angstroms. The adsorbents are said to be able to reduce $C_2$HFCs in hexafluoroethane to 10 ppm or less.

As for the purification of unsaturated compounds containing fluorine, U.S. Pat. No. 3,381,041 discloses the use of sulfuric acid and mercurial type compounds from 0 to 150° to remove olefinic impurities from saturated and unsaturated hydrofluorocarbons. However, there is no disclosure of using an adsorbent, such as a zeolite, to remove the impurities.

Despite the foregoing developments, it is desired to provide a process for purifying HFBD to a purity greater than 99.99%. It is further desired to provide such a process based on the use of an adsorbent to remove impurities. It is still further desired to provide a process for removing hydrofluorocarbon impurities and non-hydrofluorocarbon impurities, such as water, HF and/or alcohol(s), from HFBD to provide HFBD containing less than 0.01% of such impurities.

All references cited herein are incorporated herein by reference in their entireties.

BRIEF SUMMARY OF THE INVENTION

Accordingly, the invention provides a process for purifying HFBD, which process comprises: (a) contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å and said adsorbent is contacted with said HFBD at a rate of at least 2.7 kg of said HFBD per hour; and (b) recovering from said adsorbent a purified HFBD product containing at least 99.9 vol. % HFBD, a reduced amount of said impurities and less than 0.1 vol. % hexafluoro-2-butyne.

Also provided is a process comprising: (a) contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å; and (b) recovering from said adsorbent a purified HFBD product containing more than 99.96 vol. % HFBD, a reduced amount of said impurities and less than 0.04 vol. % hexafluoro-2-butyne.

Still further provided is a process comprising: (a) contacting a composition containing said HFBD with an adsorbent to remove from said HFBD at least two impurities selected from the group consisting of water, an alcohol, hydrofluoric acid and a fluorinated olefin, wherein said adsorbent is a solid provided as a bed within a column having a length of at least 30 cm and an inner diameter of at least 2.5 cm, and said contacting comprises passing a feed gas containing said HFBD over said bed; and (b) recovering from said adsorbent a purified HFBD product containing at least 99.9 vol. % HFBD, a reduced amount of said impurities and less than 0.1 vol. % hexafluoro-2-butyne.

Additionally provided is a process comprising: (a) contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å; (b) recovering from said adsorbent a purified HFBD product containing more than 99.9 vol. % HFBD, a reduced amount of said impurities and less than 0.1 vol. % hexafluoro-2-butyne; and (c) reactivating said adsorbent after said adsorbent has been spent by at least one cycle of said contacting and said recovering, wherein said reactivating comprises heating said spent adsorbent under a dry inert gas purge, and then cooling said heated adsorbent to room temperature prior to additional said contacting.

HFBD produced by the process of the invention is also provided.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Past efforts at purification of hydrofluorocarbons with adsorbents typically relied upon the reactivity of the adsorbents with the olefinic compounds as the basis for their removal. The invention is based, in part, on our surprising discovery that certain adsorbents can remove impurities from HFBD without substantially reacting with the HFBD.

Through our investigations, we have discovered that adsorption of HFBD to certain adsorbents is an exothermic process, which provides the thermal energy necessary to initiate the nucleophilic rearrangement of HFBD to hexafluoro-2-butyne (HFB). This rearrangement in turn is rapid and exothermic. Column temperatures in excess of 400° C. and pressures in excess of 60 psig are observed in a ¾" (1.91 cm) outer diameter (OD)×34" (86.4 cm) long adsorbent column within seconds. The underlying chemistry of this nucleophilic rearrangement is documented in the literature. (Miller et al., JACS 1767–1768 (Apr. 5, 1961); Weigert, 65 J.Fluorine Chem 67–71 (1993); Chambers et al., 91 J. Fluorine Chem. 63–68 (1998)). This type of behavior makes it difficult, if not impossible, to safely scale up an adsorbent bed.

Figure 1:
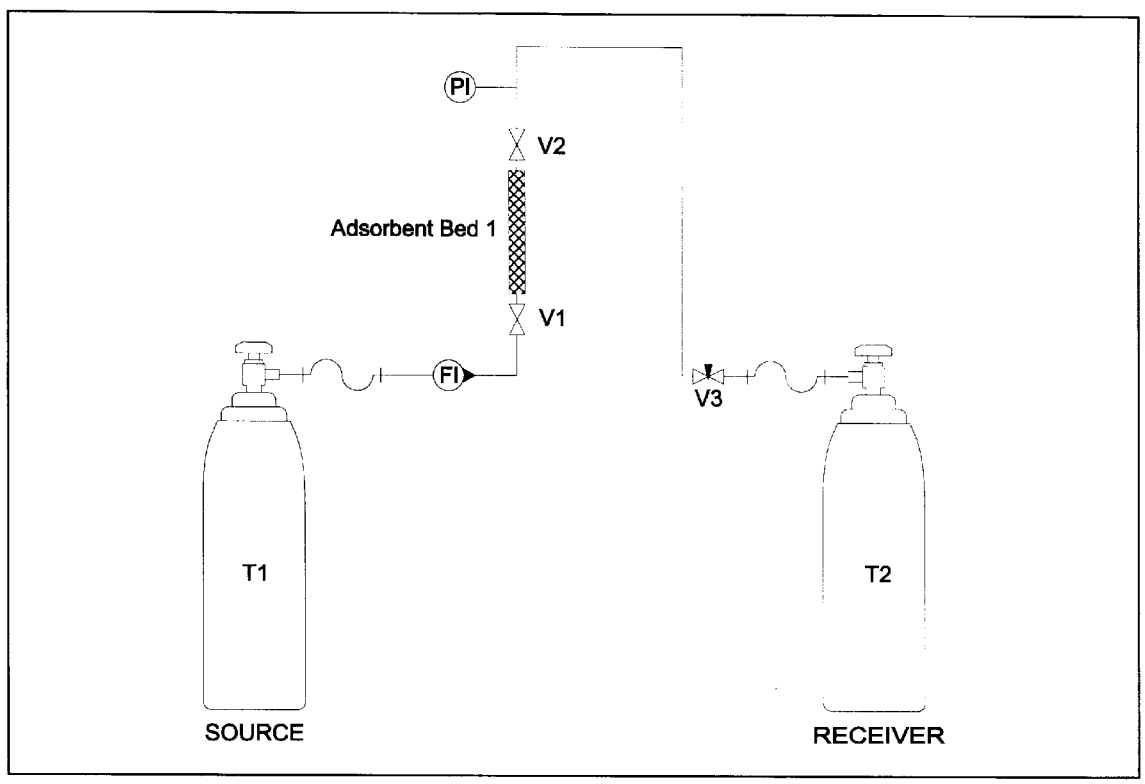
FIG. 1 is a process flow diagram of an apparatus for performing a process of the invention.

The invention makes it possible to remove from HFBD at least one impurity selected from the group consisting of water, an alcohol, HF and a perfluorinated olefin, without substantial isomerization of the HFBD to form HFB. Such impurities from the manufacture of HFBD are preferably removed by passing the product in a gaseous form over a bed of solid adsorbent that selectively removes byproducts, solvents, unreacted starting materials and partially reacted starting materials. The process flow diagram of this embodiment of the inventive process is shown in FIG. 1. Gas flows from source tank T1 past flow indicator FI, through valve V1, adsorbent bed 1, and valve V2, past pressure indicator PI, and through flow control valve V3 into receiver tank T2.

Preferred adsorbents used in the process of the present invention improve over those used previously, since the bulk component (HFBD) is excluded from the adsorbent while the impurities are adsorbed, thus producing a purified product using smaller beds and avoiding deleterious decomposition reactions from occurring. In addition, using the preferred adsorbents may allow the purification to be carried out at higher temperatures than previously possible. The improvement in HFBD purification is realized by using an adsorbent comprising small pore adsorbents that exclude HFBD. The most preferred adsorbents of the invention are molecular sieves having a controlled pore size of about 5 Å, which effectively excludes the sorption of the HFBD into the internal pore volume. Thus, adsorbents having an average pore size less than 6 Å are preferred, with adsorbents having an average pore size of 4 Å to 6 Å being more preferred and 5 Å molecular sieve being most preferred.

A variety of inorganic microporous metallosilicates containing framework elements other than aluminum will also be useful for HFBD purification. For example, the silicoaluminophosphate SAPO-42 has the same structure as Zeolite type A. The preferred crystalline aluminosilicate is typically referred to as a zeolite selected from the group consisting of structures containing 8-member oxygen ring apertures and having nominal effective pore entrances of 4 to 5 angstroms. These zeolites are typically referred to as small pore and behave as 4 Å and 5 Å type sieves, excluding molecules having effective diameters greater than 5 Å. Broadly, any metallosilicate that is stable under process conditions and excludes HFBD from the internal pore volume is suitable for use in the inventive process. Due to their availability and demonstrated utility, small pore zeolites are preferred and Type A zeolites most preferred. Preferred zeolite compositions include A-type zeolites, ZK-4, ZK-5, Chabazite, Erionite, Gmelinite, and Offretite. The zeolites can be either synthesized or naturally occurring and may be exchanged with a wide variety of cations to alter either the equilibrium affinity for the impurities or size of the small pore opening to the zeolite. For example, it is well known that the pore size of NaA zeolite (referred to as 4A type) can be modified by replacing the majority of the Na cations with Ca by conventional ion exchange methods. The resulting CaA zeolite is referred to as 5A type and will sorb molecules that are excluded from NaA.

Figure 2:
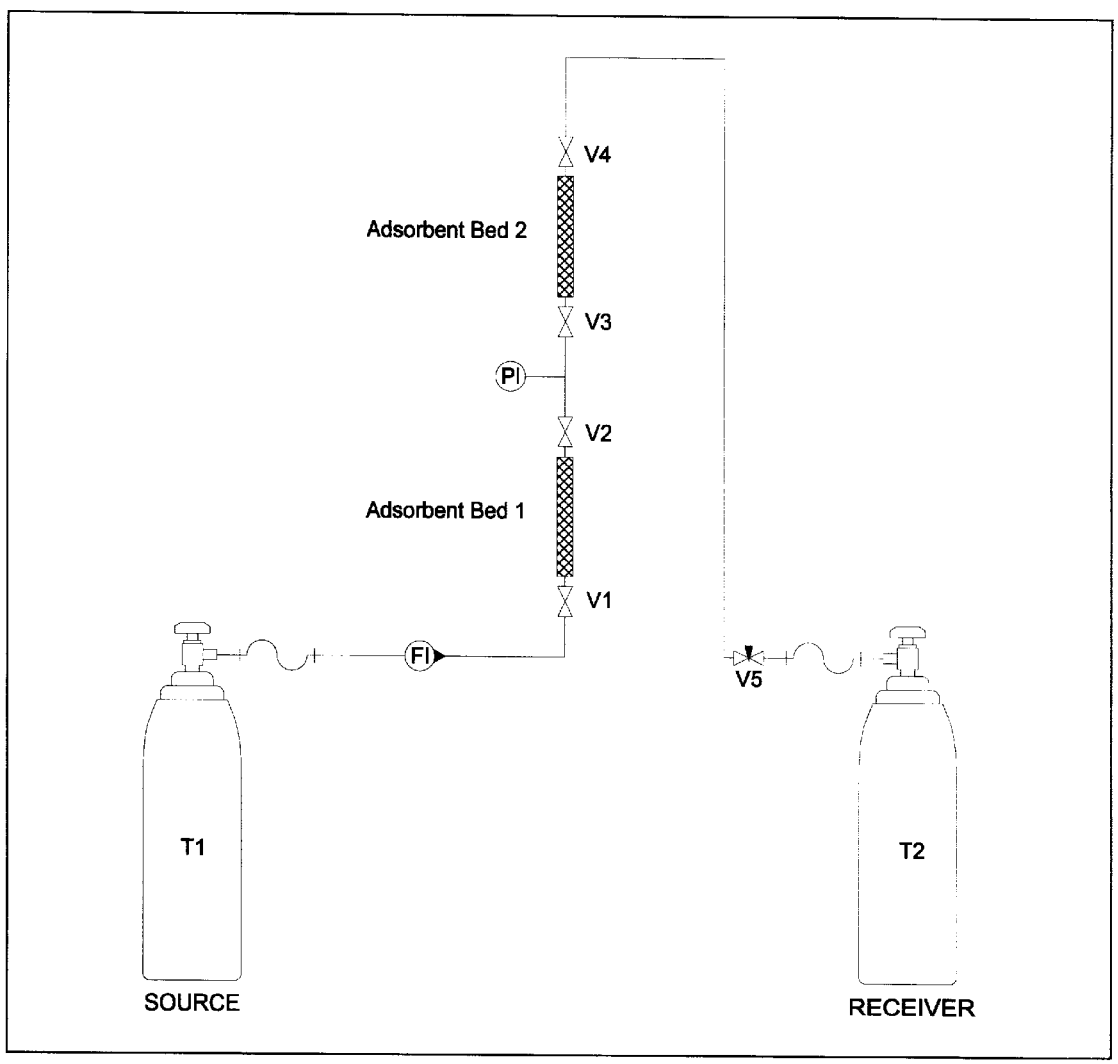
FIG. 2 is a process flow diagram of another apparatus for performing an alternative embodiment of the process of the invention.

Other less preferred adsorbents can be used in conjunction with the HFBD-excluding adsorbent to remove various impurities from the process stream. Such adsorbents include, but are not limited to, 3 Å molecular sieve, 13X molecular sieve, activated carbon, NaF, activated alumina, and mixtures thereof. We have found that the purest product is obtained when a bed of 13X, preferably containing about 0.5 to 2.5 wt. % water, is placed upstream of a bed containing 5 Å molecular sieve. The process flow diagram of this embodiment of the invention is shown in FIG. 2. Gas flows from source tank T1 past flow indicator FI, through valve V1, adsorbent bed 1 containing 13X molecular sieve and valve V2, past pressure indicator PI, through flow control valve V3, adsorbent bed 2 containing 5 Å molecular sieve, and valves 4 and 5 into receiver tank T2.

Upon scaling this process beyond the ¼" OD (0.64 cm OD and 0.46 cm ID or inner diameter) bed size, it was found that almost all of the adsorbents screened will catalyze the rearrangement of HFBD to 1,1,1,4,4,4-Hexafluoro-2-butyne. This was accompanied by rapid pressure and temperature increases. However, 5 Å molecular sieve was successful in delivering the desired purity levels without catalyzing the rearrangement reaction. Additional preferred adsorbents of the invention can be identified by their ability to maintain the temperature of the bed at or below about 35° C. while the bed is contacting the HFBD containing feed gas and producing purified HFBD product.

Thus a preferred purification process of the invention comprises the use of a 5 Å molecular sieve as follows. A 5 Å molecular sieve adsorbent trap (i.e., adsorbent bed 1 of FIG. 1) is prepared by loading and then activating under high temperature and dry nitrogen purge. Bed temperatures greater than 500° F. (260° C.) during activation are preferred. The trap is then allowed to cool to room temperature before the purification step. The same procedure can be used to reactivate a spent bed after multiple purification cycles. The 5 Å molecular sieve activation step may be skipped if moisture removal is not important to the ultimate consumer of the purified HFBD. Source tank T1 is then connected to the front end of adsorbent bed 1, and the tank and bed are then evacuated by a vacuum pump. Once the system is leak-tight and under less than 0.02 Torr (2.7 Pa) absolute pressure, the temperature of receiver tank T2 is then lowered below that of source tank T1. Temperatures of −100° F. to 32° F. (−73.3° C. to 0° C.) are preferred. Lower (e.g., liquid nitrogen) and higher temperatures will work as long as the temperature in source tank T1 is higher than the temperature in receiver tank T2, but are less preferred.

With flow control valve V3 closed, the source cylinder is opened and the system at pressure indicator P1 is brought up to the source tank's vapor pressure. Pressures of 10 to 15 psig (69 to 103 kPa) have been observed. Collection of purified product is then started by opening flow control valve V3 and monitoring flow with flow indicator FI. Flows are preferably maintained between 1.5 to 8.0 lbs/hr (0.68 to 3.6 kg/hr). Higher flow rates are more preferred and lower flow rates are less preferred based on economic considerations. In certain embodiments, the flow rate is greater than 2.67 kg/hr, preferably greater than 3 kg/hr.

System pressure observed at pressure indicator PI dictates the maximum flow attainable and is maintained above −4 psig (−28 kPa), preferably 1 to 4 psig (6.9 to 28 kPA) during the process by reducing the flow rate via flow control valve V3. The purification will work at lower pressures, albeit at the sacrifice of the capacity of the 5 Å molecular sieve bed. The purification is terminated when (1) the receiver tank is full, (2) the 5 Å molecular sieve bed is spent and/or (3) when the source tank is empty. Receiver tank T2 is then isolated and warmed to room temperature.

In preferred embodiments of the invention, the bed is loaded in a column, preferably a stainless steel column, having an OD greater than 0.635 cm, preferably at least 2.7 cm. The column (and the bed within it) has a preferred length of at least 30 cm and a preferred ID of at least 2.5 cm, more preferably at least 5.1 cm. The bed preferably comprises 5 Å molecular sieve or the like as the solid adsorbent. The properties of 5 Å with respect to HFBD have allowed us to safely scale-up the purification process to meet the low impurity levels desired by the semiconductor industry.

The invention enables the production of HFBD having a purity greater than 99.9 vol. %, preferably greater than 99.96%. Typical impurities removed include, but are not limited to, water, alcohols (e.g., isopropanol, etc.), HF and organics, such as fluorinated olefins, methanes, ethanes, ethynes, propanes, propynes, butanes and butynes. Typical fluorinated olefins removed include, but are not limited to, $C_2$ fluorocarbon ethylenes, $C_2$ chlorofluorocarbon ethylenes, $C_2$ hydrofluorochlorocarbon ethylenes, $C_3$ fluorocarbon propenes, $C_3$ chlorofluorocarbon propenes, $C_3$ hydrofluorochlorocarbon propenes, $C_4$ fluorocarbon butenes and butadienes, $C_4$ chlorofluorocarbon butanes and butadienes, and $C_4$ hydrofluorochlorocarbon butenes and butadienes.

The concentration of water in the purified HFBD product is preferably at least 100 ppm lower, preferably at least 1000 ppm lower than in the impure HFBD feedstock.

The concentration of alcohol in the purified HFBD product is preferably at least 10 ppm lower, preferably at least 100 ppm lower than in the impure HFBD feedstock.

The concentration of fluorinated olefin in the purified HFBD product is preferably at least 10 ppm lower, preferably at least 100 ppm lower than in the impure HFBD feedstock.

The concentration of HF in the purified HFBD product is preferably at least 10 ppm lower, preferably at least 100 ppm lower, than in the impure HFBD feedstock.

Purification is accomplished without producing substantial amounts of hexafluoro-2-butyne. In particularly preferred embodiments, the purified HFBD product contains less than 0.1 vol. %, more preferably less than 0.04 vol. % hexafluoro-2-butyne.

The invention will be illustrated in more detail with reference to the following Examples, but it should be understood that the present invention is not deemed to be limited thereto.

EXAMPLES

Hexafluoro-1,3-butadiene ($C_4F_6$) is commercially available from three suppliers: Ausimont (Thorofare, N.J.), PCR/Lancaster (Windham, N.H.), and American Gas Products (Russian source), with Ausimont being most preferred. Source cylinders have ranged from 5 lb (2.3 kg) to 110 lb (50 kg) in maximum fill size. Samples of the highest purity product available from each supplier were analyzed by GC-MS, GC-AED, and GC-FTIR. Based on Carbon 179 nm area counts from the GC-AED analysis, none of the products exceeded purities greater than 99.9 vol %.

If inert gas levels are high, then they are removed by a procedure known as blowdown or controlled venting. The blowdown procedure was shown not to have any positive effect on impurities other than inerts (nitrogen and oxygen).

The 5 Å molecular sieve trap used in Examples 1–3 was activated as follows.

1.6 lbs (0.73 kg) of 5 Å molecular sieve (Advanced Specialty Gas Equipment, Middlesex, N.J.) were loaded into a 2" (5.08 cm) ID by 16" (40.64 cm) long stainless steel cylinder having a wall thickness of about 0.093" (0.236 cm). The bed was connected to a dry nitrogen source with a flow of 50 to 500 sccm. The bed temperature was raised to 500° F. (260° C.). After 24 hours, the nitrogen purge was stopped, the heat source turned off and the bed was evacuated with a vacuum pump to less than 1 Torr (133 Pa) until the bed temperature reached room temperature.

Example 1

Purification of 88 lb/40 kg of HFBD with 5 Å Molecular Sieve

Referring to FIG. 1, a 110 lb (49.9 kg) cylinder of HFBD supplied from Ausimont, whose inerts had been removed by controlled venting, was employed as source tank T1. The system was evacuated to 0.02 Torr (2.7 Pa) and receiver tank T2 was lowered to −100° F. (−73.3° C.) by using dry ice. The control valve was then used to maintain a system pressure of greater than −4 psig (−28 kPa) and a flow rate of less than or equal to 8 lbs/hr (3.6 kg/hr). After 6 hours, the transfer was complete and receiver tank T2 was isolated and removed. A subsequent receiver tank was connected and the system, including the 5 Å molecular sieve bed, was evacuated to less than 0.02 Torr (2.7 Pa). While not necessary, it has been observed that evacuating the 5 Å molecular sieve bed between fills extends its lifetime. The procedure was repeated until four receiver tanks had been filled to 22 lb (10 kg) each. The composition in source tank T1 before transfill and the compositions of the purified material in the four receiver tanks are shown in Table 1, below. Product purities of greater than 99.99% were obtained.

TABLE 1

Compositions of feed and product gases of Example 1.

| Species | Source (110 lb/ 50 kg) | Receiver No. 1 (22 lb/10 kg) | Receiver No. 2 (22 lb/10 kg) | Receiver No. 3 (22 lb/10 kg) | Receiver No. 4 (22 lb/10 kg) |
|---|---|---|---|---|---|
| Ne | 0 | 0 | 0 | 0 | 0 |
| Ar | 75.4 | 0 | 0 | 5.4 | 1.6 |
| $N_2$ | 175.6 | 6.5 | 2.0 | 6.6 | 2.2 |
| $CH_4$ | 10.7 | 0 | 0 | 2.0 | 0.7 |

TABLE 1-continued

Compositions of feed and product gases of Example 1.

| Species | Source (110 lb/ 50 kg) | Receiver No. 1 (22 lb/10 kg) | Receiver No. 2 (22 lb/10 kg) | Receiver No. 3 (22 lb/10 kg) | Receiver No. 4 (22 lb/10 kg) |
|---|---|---|---|---|---|
| CO | 0 | 0 | 0 | 0 | 0 |
| Hexafluoro-2-butyne | 54.4 | 25.6 | 30.0 | 33.1 | 31.2 |
| Propylene | 11.4 | 24.6 | 20.7 | 30.8 | 27.8 |
| $C_4$ FC | 30.0 | 63.3 | 1.6 | 6.0 | 11.2 |
| IPA | 0 | 0 | 0 | 0 | 0 |
| $C_4$CFC | 13.8 | 6.4 | 0 | 0 | 0 |
| $C_8F_{12}$ | 0 | 0 | 0 | 0 | 0 |
| $H_2O$ | 250 | 10 | 10 | 10 | 10 |
| HF | 1 | 1 | 1 | 1 | 1 |
| TOTAL ($ppm_v$) | 622.3 | 137.6 | 65.3 | 94.9 | 85.7 |
| Purity (volume %) | 99.938 | 99.986 | 99.993 | 99.991 | 99.992 |

Example 2

Purification of 99 lb/45 kg HFBD with 5 Å Molecular Sieve

Referring again to FIG. 1, a 110 lb cylinder of HFBD supplied from Ausimont, whose inerts have been removed by controlled venting, was employed as source tank T1. The system was evacuated to 0.02 Torr and the receiver tank T2 was lowered to −100° F. (−73.3° C.) by using dry ice. The control valve was then used to maintain a system pressure of greater than −4 psig (−28 kPa) and a flow rate of less than or equal to 8 lbs/hr (3.6 kg/hr). In eight-hour intervals the transfer was interrupted. During that time the source and receiver tanks T1 and T2 were closed and isolated. The rest of the system including the adsorbent bed was evacuated. The transfer was resumed the following morning and continued until the receiver tank was full. This particular transfer took three eight-hour cycles to complete. While not necessary, it has been observed that evacuating the 5 Å molecular sieve bed between fills extends the lifetime. The composition in the source tank before transfill and the composition of the purified material in the receiver tank are shown in Table 2, below. A product purity of greater than 99.98% was obtained.

TABLE 2

Composition of feed and product gases of Example 2.

| Species | Source Tank (110 lb/50 kg) | Receiver Tank (99 lb/10 kg) |
|---|---|---|
| Ne | 0 | 0 |
| Ar | 65.7 | 0 |
| $N_2$ | 163.6 | 7.9 |
| $CH_4$ | 0 | 0 |
| CO | 0 | 0 |
| Hexafluoro-2-butyne | 3.3 | 139.9 |
| Propylene | 99.7 | 0 |
| $C_4$ FC | 65.9 | 1.55 |
| IPA | 12.4 | 0 |
| $C_4$CFC | 7.16 | 24.9 |
| $C_8F_{12}$ | 0 | 0.7 |
| $H_2O$ | 350 | 10 |
| HF | 1 | 1 |
| TOTAL ($ppm_v$) | 768.8 | 186.6 |
| Purity (volume %) | 99.92 | 99.982 |

Example 3

Purification of HFBD with 5 Å Molecular Sieve with Fractional Collection

Referring again to FIG. 1, a 110 lb cylinder of HFBD supplied from Ausimont, whose inerts have been removed by controlled venting, was employed as source tank T1. The system was evacuated to 0.02 Torr and the receiver tank T2 was lowered to −100° F. (−73.3° C.) by using dry ice. The control valve was then used to maintain a system pressure of greater than −4 psig (−28 kPa) and a flow rate of less than or equal to 8 lbs/hr (3.6 kg/hr). Over twenty different receiver tanks sized from 2 lb (0.91 kg) to 20 lb (9.1 kg) were filled from this receiver. We selected for analysis three successive receiver tank fills at random during the course of emptying the source cylinder. In between each receiver tank fill, the source and receiver tanks were closed and isolated. The rest of the system, including the adsorbent bed, was evacuated. The transfer was then resumed. The composition in the source tank before transfill and the compositions of the purified material in the three receiver tanks are shown in Table 3, below. Product purities of greater than 99.98% were obtained.

TABLE 3

Composition of feed and product gases of Example 3.

| Species | Source (110 lb/50 kg) | Receiver No. 1 (5 lb/2.3 kg) | Receiver No. 2 (2 lb/0.91 kg) | Receiver No. 3 (2 lb/0.91 kg) |
|---|---|---|---|---|
| Ne | 0 | 0 | 0 | 0 |
| Ar | 35.6 | 1.4 | 0 | 0 |
| $N_2$ | 160.0 | 8.8 | 18.8 | 15.0 |
| $CH_4$ | 6.7 | 33 | 0 | 19.3 |
| CO | 0 | 0 | 0 | 0 |
| Hexafluoro-2-butyne | 1.9 | 29.1 | 15.0 | 41.4 |
| Propylene | 29.4 | 17.3 | 22.8 | 8 |
| $C_4$ FC | 109.6 | 6.0 | 9.0 | 30.7 |
| IPA | 0 | 0 | 0 | 0 |
| $C_4$CFC | 14.9 | 0 | 0 | 0 |
| $C_8F_{12}$ | 0.8 | 0 | 0 | 0 |
| $H_2O$ | 150 | 10 | 10 | 10 |
| HF | 1 | 1 | 1 | 1 |
| TOTAL ($ppm_v$) | 509.9 | 107.6 | 76.6 | 125.4 |
| Purity (volume %) | 99.949 | 99.989 | 99.992 | 99.987 |

Comparative Example 4

Purification of HFBD with 13X 1.9 lbs (0.86 kg) of 13X molecular sieve were loaded into a 2" (5.08 cm) ID by 16" (40.64 cm) long stainless steel cylinder having a wall thickness of about 0.093" (0.236 cm). The bed was connected to a dry nitrogen source with a flow of 50 to 500 sccm. The bed temperature was raised to 500° F. (260° C.). After 24 hours, the nitrogen purge was stopped, the heat source turned off and the bed was evacuated with a purge was stopped, the heat source turned off and the bed was evacuated with a vacuum pump to less than 1 Torr (133 Pa) until the bed temperature reached room temperature. 31 grams of the resulting activated 13X were then transferred into a ¾" OD (1.9 cm OD and 1.6 cm ID)×18" (46 cm) long stainless steel tube for purification of HFBD.

Referring again to FIG. 1, commercial grade HFBD was employed as source tank T1. The system was evacuated to 0.02 Torr and the receiver tank T2 was lowered to −100° F. (−73.3° C.) by using dry ice. With flow control valve V3 closed, source tank T1 was opened and flow to the bed was started at 3 gms/hr in an attempt to keep the bed temperature below 80° F. (27° C.) during the conditioning phase ($C_4F_6$ adsorption). After 25 minutes, the bed temperature rapidly climbed to 150° F. (66° C.). At this point, analytical sampling revealed that the material had completely isomerized to hexafluoro-2-butyne. This type of isomerization process was also observed with alumina, activated carbons, and other large pore molecular sieves, such as sodium mordenite.

While the invention has been described in detail and with reference to specific examples thereof, it will be apparent to one skilled in the art that various changes and modifications can be made therein without departing from the spirit and scope thereof.

What is claimed is:

1. A process for purifying hexafluoro-1,3-butadiene (HFBD), said process comprising:
    contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å and said adsorbent is contacted with said HFBD at a rate of at least 2.7 kg of said HFBD per hour; and
    recovering from said adsorbent a purified HFBD product containing at least 99.9 vol. % HFBD, a reduced amount of said impurities and less than 0.1 vol. % hexafluoro-2-butyne.

2. The process of claim 1, wherein said average pore diameter of said adsorbent is 4 Å to 6 Å.

3. The process of claim 1, wherein said adsorbent is 5 Å molecular sieve.

4. The process of claim 3, wherein said adsorbent is provided as a bed within a column, and said contacting comprises passing a feed gas containing said HFBD over said bed.

5. The process of claim 4, wherein said column has an inside diameter of at least 2.5 cm.

6. The process of claim 5, wherein said bed has an outside diameter of at least 2.7 cm and a length of at least 30 cm.

7. The process of claim 4, wherein a column pressure within said column during said contacting is from 69 to 103 kPa.

8. The process of claim 4, wherein a receiver tank temperature of said purified HFBD product during said recovering is −74° C. to 0° C., and wherein said receiver tank temperature is lower than a feed gas temperature of said feed gas.

9. The process of claim 4, wherein a bed temperature of said bed never exceeds 35° C. during said contacting and said recovering.

10. The process of claim 4, further comprising activating said adsorbent prior to said contacting, wherein said activating comprises heating said bed to about 260° C. under a dry nitrogen purge, and then cooling said bed to room temperature prior to said contacting.

11. The process of claim 4, further comprising reactivating said adsorbent after said adsorbent has been spent by at least one cycle of said contacting and said recovering, wherein said reactivating comprises heating said spent adsorbent to about 260° C. under a dry nitrogen purge, and then cooling said heated adsorbent to room temperature prior to said contacting.

12. The process of claim 1, wherein said water, said alcohol and said fluorinated olefin are removed from said HFBD.

13. The process of claim 1, wherein a concentration of water in said purified HFBD product is at least 100 ppm lower than in said composition containing HFBD, and a concentration of said fluorinated olefin in said HFBD product is at least 10 ppm lower than in said composition containing HFBD.

14. The process of claim 1, wherein a concentration of alcohol in said purified HFBD product is at least 10 ppm lower than in said composition containing HFBD, and a concentration of said fluorinated olefin in said HFBD product is at least 10 ppm lower than in said composition containing HFBD.

15. The process of claim 14, wherein said alcohol is isopropanol.

16. The process of claim 14, wherein said fluorinated olefin is at least one member selected from the group consisting of $C_2$ fluorocarbon ethylenes, $C_2$ chlorofluorocarbon ethylenes, $C_2$ hydrofluorochlorocarbon ethylenes, $C_3$ fluorocarbon propenes, $C_3$ chlorofluorocarbon propenes, $C_3$ hydrofluorochlorocarbon propenes, $C_4$ fluorocarbon butenes and butadienes, $C_4$ chlorofluorocarbon butanes and butadienes, and $C_4$ hydrofluorochlorocarbon butenes and butadienes.

17. The process of claim 1, wherein said rate is at least 3 kilograms of HFBD per hour.

18. The process of claim 1, wherein said purified HFBD product contains less than 0.01 vol. % hexafluoro-2-butyne.

19. The process of claim 1, wherein said composition containing said HFBD is contacted with more than one said adsorbent, and wherein said composition is first contacted with 13X molecular sieve adsorbent containing at least 0.5 wt. % water and then contacted with 5 Å molecular sieve adsorbent.

20. The process of claim 1, wherein said purified HFBD product contains more than 99.96 vol. % HFBD.

21. A process for purifying hexafluoro-1,3-butadiene (HFBD), said process comprising:

contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å; and recovering from said adsorbent a purified HFBD product containing more than 99.96 vol. % HFBD, a reduced amount of said impurities and less than 0.04 vol. % hexafluoro-2-butyne.

22. The process of claim 21, wherein said adsorbent is provided as a bed within a column having an length of at least 30 cm and an inner diameter of at least 2.5 cm, and said contacting comprises passing a feed gas containing said HFBD over said bed.

23. The process of claim 22, wherein said adsorbent is contacted with said HFBD at a rate of at least 2.7 kg of said HFBD per hour.

24. process for purifying hexafluoro-1,3-butadiene (HFBD), said process comprising:

contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å and is provided as a bed within a column having an length of at least 30 cm and an inner diameter of at least 2.5 cm, and said contacting comprises passing a feed gas containing said HFBD over said bed; and recovering from said adsorbent a purified HFBD product containing at least 99.9 vol. % HFBD, a reduced amount of said impurities and less than 0.1 vol. % hexafluoro-2-butyne.

25. A process for purifying hexafluoro-1,3-butadiene (HFBD), said process comprising:

contacting a composition containing said HFBD with an adsorbent to remove from said HFBD at least two impurities selected from the group consisting of water, an alcohol, hydrofluoric acid and a fluorinated olefin, wherein said adsorbent is a solid having an average pore diameter of about 5 Å;

recovering from said adsorbent a purified HFBD product containing at least 99.9 vol. % HFBD, a reduced amount of said impurities and less than 0.1 vol. % hexafluoro-2-butyne; and reactivating said adsorbent after said adsorbent has been spent by at least one cycle of said contacting and said recovering, wherein said reactivating comprises heating said spent adsorbent under a dry inert gas purge, and then cooling said heated adsorbent to room temperature prior to additional said contacting.

* * * * *